(12) United States Patent
Lehnherr et al.

(10) Patent No.: US 9,861,667 B2
(45) Date of Patent: Jan. 9, 2018

(54) **BACTERIOPHAGES AGAINST *SALMONELLA* SSP AND THEIR USE**

(71) Applicant: PTC PHAGE TECHNOLOGY CENTER GMBH, Boenen (DE)

(72) Inventors: Hansjoerg Lehnherr, Bern (CH); Tatiana Lehnherr-Ilina, Hamm (DE)

(73) Assignee: PTC Phage Technology Center GmbH, Boenen (DE)

( * ) Notice: Subject to any disclaimer, the term of this patent is extended or adjusted under 35 U.S.C. 154(b) by 0 days.

(21) Appl. No.: 14/777,758

(22) PCT Filed: May 18, 2014

(86) PCT No.: PCT/EP2014/055404
§ 371 (c)(1),
(2) Date: Sep. 17, 2015

(87) PCT Pub. No.: WO2014/147063
PCT Pub. Date: Sep. 25, 2014

(65) Prior Publication Data
US 2016/0296571 A1    Oct. 13, 2016

(30) Foreign Application Priority Data

Mar. 18, 2013 (EP) .................................... 13159756

(51) Int. Cl.
*C12N 7/00* (2006.01)
*A61K 35/76* (2015.01)
*C12Q 1/70* (2006.01)

(52) U.S. Cl.
CPC .............. *A61K 35/76* (2013.01); *C12N 7/00* (2013.01); *C12Q 1/701* (2013.01); *C12N 2795/00033* (2013.01); *C12N 2795/10121* (2013.01); *C12N 2795/10132* (2013.01); *C12N 2795/10321* (2013.01); *C12N 2795/10332* (2013.01)

(58) Field of Classification Search
None
See application file for complete search history.

(56) References Cited

U.S. PATENT DOCUMENTS

2011/0005254 A1   3/2011   Shin et al.

FOREIGN PATENT DOCUMENTS

WO    2013014273 A1    1/2013
WO    2013024304 A1    2/2013

OTHER PUBLICATIONS

Zhang et al., "Development of an Anti-*Salmonella* Phage Cocktail with Increased Host Range", Foodborne Pathogens and Disease, Jan. 1, 2010, vol. 7, No. 11, p. 1415-1419.
Kocharunchitt et al., "Use of Bacteriophages as Biocontrol Agents to Control *Salmonella* Associated with Seed Sprouts", International Journal of Food Microbiology, Jan. 1, 2009, vol. 128, p. 453-459.
Krylov et al., "Ambivalent Bacteriophages of Different Species Active on *Escherichia coli* K12 and *Salmonella* sp. Strains", Russian Journal of Genetics, Jan. 1, 2006, vol. 42, No. 2, p. 106-114.

*Primary Examiner* — Michelle S Horning
(74) *Attorney, Agent, or Firm* — Whitham, Curtis & Cook, P.C.

(57) ABSTRACT

In a first aspect, the present invention relates to new compositions comprising new bacteriophages allowing the prophylactic or therapeutic treatment of *Salmonella* infections in mammals and birds. Moreover, the present invention relates to the method for fighting *Salmonella* comprising the step of treating matter suspected to be afflicted with *Salmonella* with the bacteriophages according to the present invention. Moreover, the present invention relates to a method of treating or preventing *Salmonella* infection, in particular, in livestock.

15 Claims, 3 Drawing Sheets

Figure 1. PCR identification assay with primer set 1
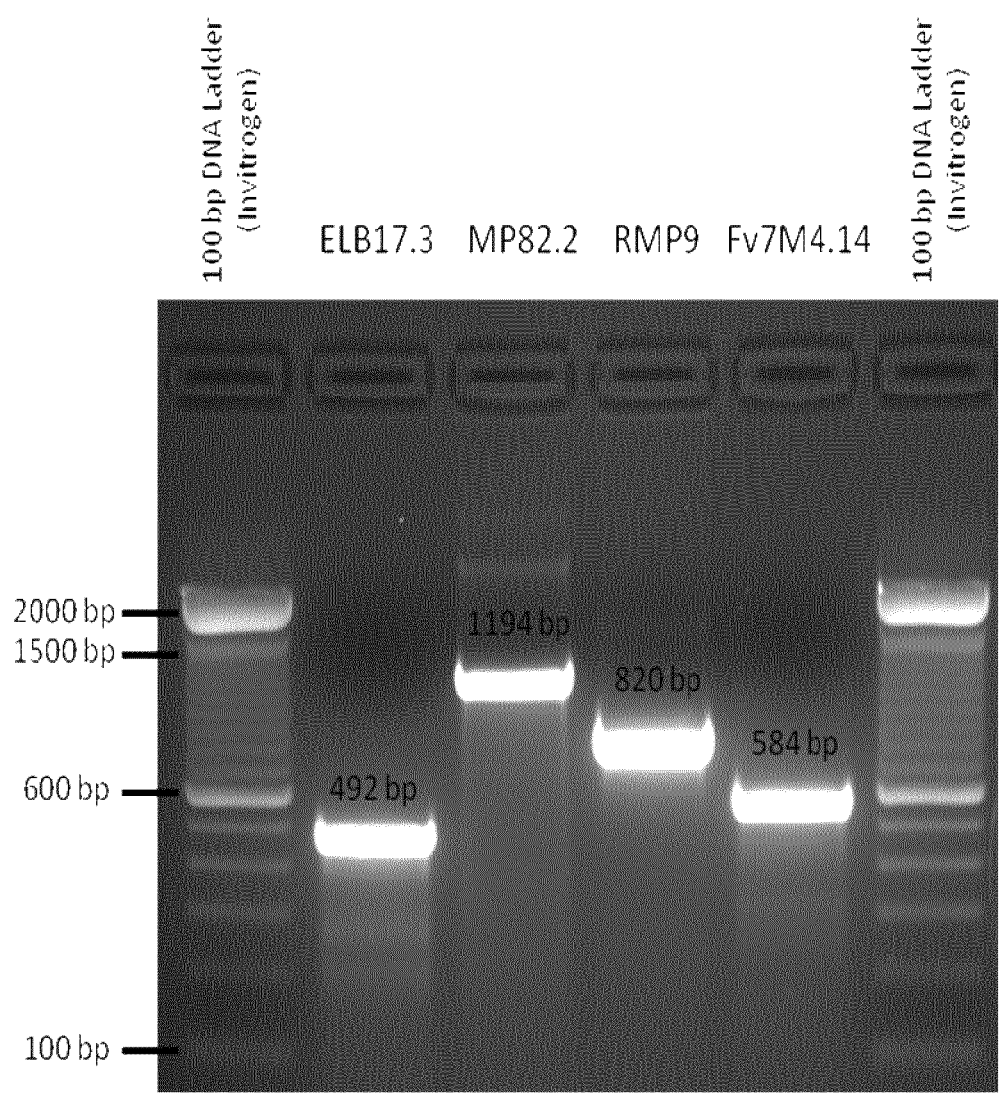

Figure 2. PCR identification assay with primer set 2
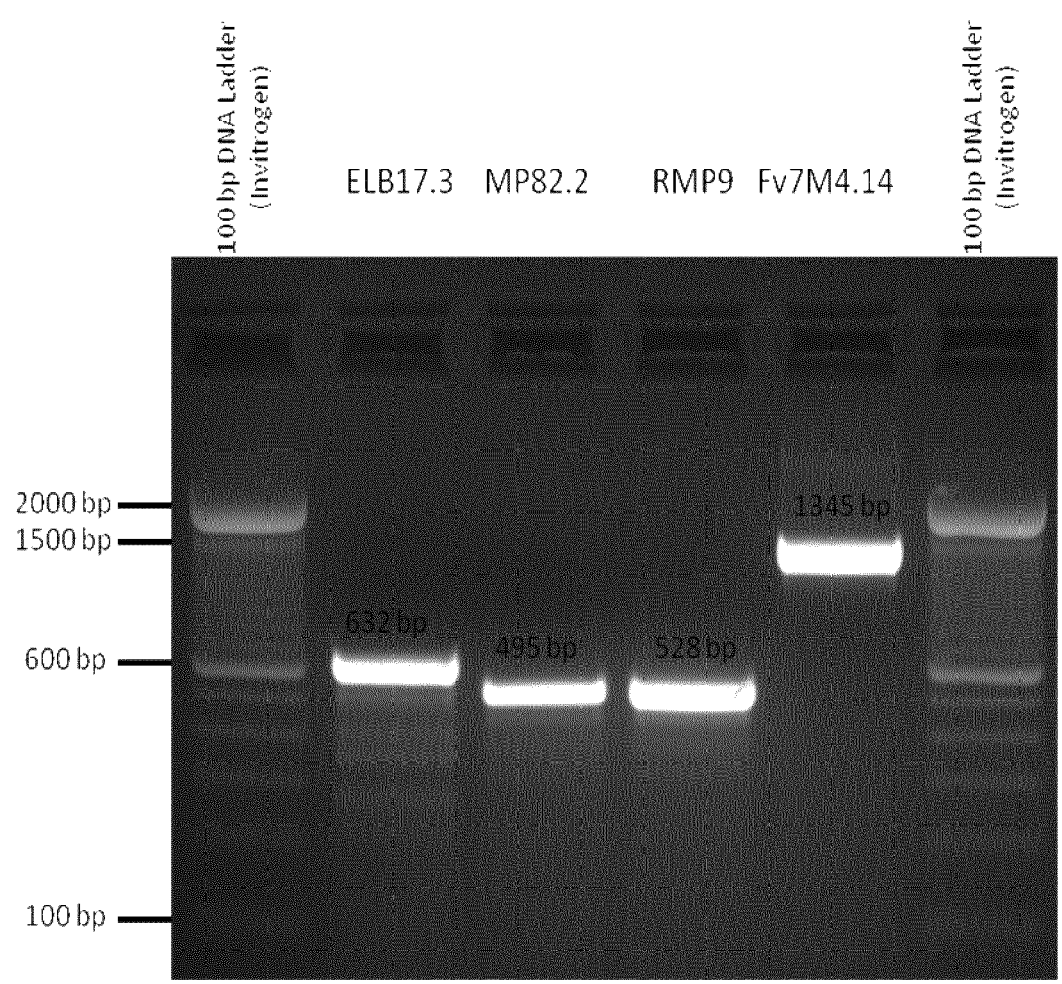

Figure 3. *Salmonella* growth inhibition assay using a single phage
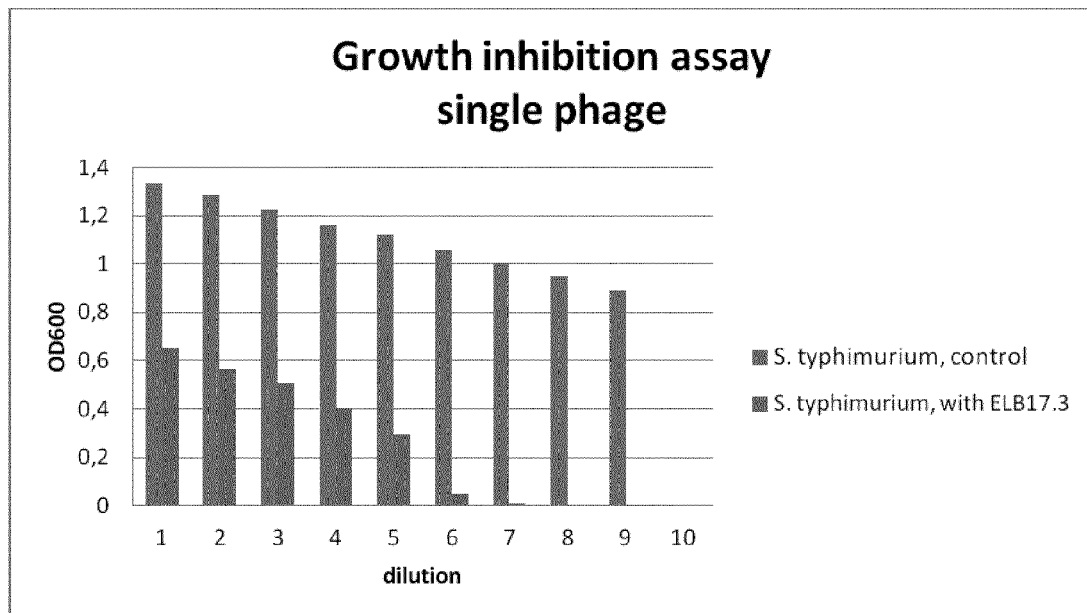
Figure 4
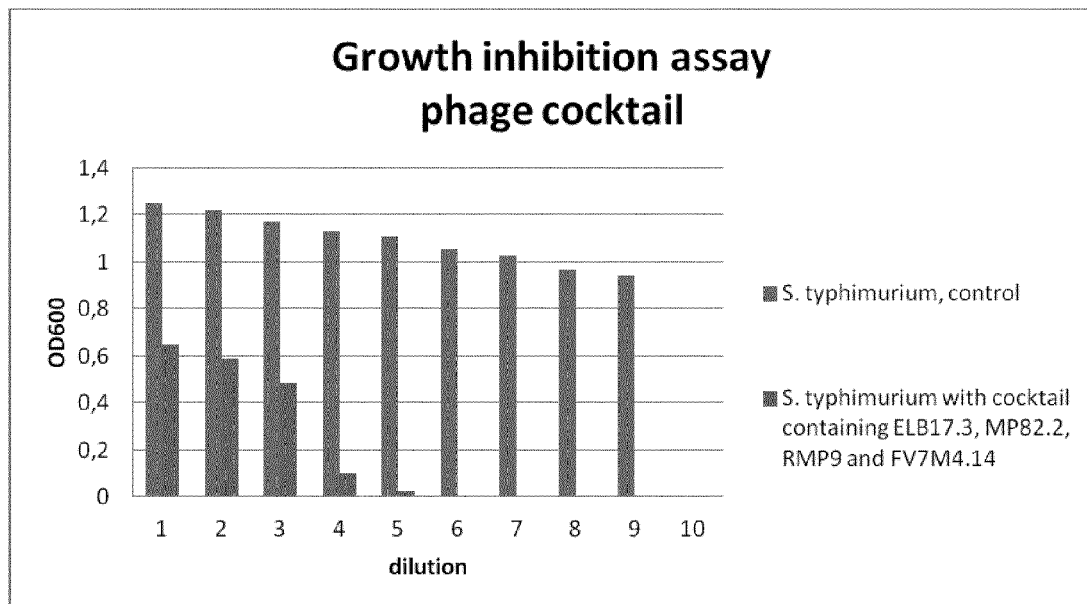

BACTERIOPHAGES AGAINST *SALMONELLA* SSP AND THEIR USE

In a first aspect, the present invention relates to new compositions comprising new bacteriophages as nutritional supplement or feed supplement, in particular, for livestock, or a feed additive or feed processing aid. Further, the present invention relates to new compositions comprising new bacteriophages allowing the prophylactic or therapeutic treatment of *Salmonella* infections in mammals and birds. Moreover, the present invention relates to the method for fighting *Salmonella* comprising the step of treating matter suspected to be afflicted with *Salmonella* with the bacteriophages according to the present invention. Moreover, the present invention relates to a method of treating or preventing *Salmonella* infection, in particular, in livestock.

BACKGROUND OF THE INVENTION

The World Health Organization annually reports several million cases of food poisoning caused by *Salmonella* spp. In 2009 the European Food Safety Authority reported over 100,000 cases, indicating that the problems with *Salmonella* spp. are not confined to developing countries and threshold countries alone.

*Salmonella* spp. are zoonotic germs, meaning they are transferred from animals or animal products to humans. The most common sources of *Salmonella* spp. in our diet are fresh poultry meat, fresh pig meat, eggs as well as fresh milk. Between 3% and 5% of the registered cases of human salmonellosis have been associated with exposure to exotic pets such as turtles, snakes, iguanas and lizards (Rabsch et al. 2003, CDC. *Salmonella* surveillance: annual summary).

This threat to consumer health lead the EC legislative authorities to release the EC regulation number 2160/2003 on the control of *Salmonella* and other specified food-borne zoonotic agents. This regulation sets a threshold level "absence in 25 grams" for fresh poultry meat for the currently most pre-dominant human pathogenic *Salmonella* species *Salmonella enterica* spp. *enterica serovar enteritidis* (short *Salmonella enteritidis* or *S. enteritidis*; further in the text the short designations are used) and *Salmonella typhimurium*.

The pressure to reduce the prevalence of these harmful pathogens is shared by all parties involved in food production. However, the currently used strategies to avoid, reduce and treat *Salmonella* spp. in the primary meat production, in slaughterhouses and in meat processing facilities are not efficient. Even strict adherence to state of the art hygiene regulations cannot prevent *Salmonella* outbreaks as the case numbers reported above demonstrate.

A commonly used method to avoid *Salmonella* spp. infection in livestock and poultry was the use of antibiotic growth promoters. At least 8 antibiotic growth promoters could be found among the "approved animal drug products" on the web site of the US FDA, with indications for use to increase weight gain or prevent infection. However, since the 1960s scientific evidence pointed out that the development of bacterial resistance to antibiotics is linked to the use of antibiotics in animal feed. In the course of the fight against bacterial antibiotic resistance the WHO issued a number of recommendations to its member-states, which included:

the termination of the use of any antimicrobial growth promoter if the same or a related product is also used in human medicine;

the replacement of antimicrobial growth promoters with non-antibiotic alternatives;

only authorised use of antimicrobial growth promoters;

monitoring of the amounts of antimicrobial growth promoters used for risk assessment purposes.

Current EU law bans the preventive use of antibiotics in farm animals. The therapeutic use of antibiotics, while still legal and applied liberally, does not result in *salmonella*-free animals either, due to the increased number of *Salmonella* ssp. isolates which are resistant against the antibiotics in use.

In the 1990s a vaccination approach to prevent bacterial infections in domestic animals has been developed. Currently, a number of commercially available vaccines (both live attenuated and inactivated) are in use to protect pigs, horses, cattle, chicken and turkey against *Salmonella Newport, Salmonella gallinarum, Salmonella enteritidis, Salmonella choleraesuis* and *Salmonella typhimurium*. Five clinical trials and 23 challenge studies have been done to evaluate the efficacy of vaccination to reduce *Salmonella* prevalence in live and slaughtered swine (Denagamage et al. 2007. Foodborne Pathog. Dis. 4:539-49) and the available evidence suggests that vaccination is associated with reduced *Salmonella* prevalence in swine at or near harvest. In poultry vaccination against *Salmonella* of laying hens, broilers and breeders was found effective and decreases the level on farm contamination as well (Berghaus et al. 2011, J. Food Prot. 74:727-34.) However, vaccination also has some drawbacks, especially when considering short lived animals like broilers. First, the immune system of chicks is developing slowly. The protection granted by a vaccination does not cover a period of several days after hatching, in which the chicks unfortunately are very susceptible to infections by *Salmonella* spp. Second, most vaccines provide protection against a single *Salmonella* species, cross protection against several isolates is rare. Thus, there is an inherent risk that a secondary *Salmonella* infection might break out despite vaccination against a first. Accordingly, there is still a high demand for alternative methods to fight *Salmonella* spp to replace the use of antibiotic growth promoters and complement the vaccination approach.

The idea to use bacteriophages to fight pathogenic bacteria is known for a long time. Indeed, already the co-discoverer of bacteriophages, Félix d'Hérelle, used bacteriophages to treat various bacterial infections almost a century ago. Since then numerous studies, experiments and therapeutic treatments, many of which were performed in the countries of the former Eastern Bloc, provided ample evidence for the safety, efficiency and efficacy of bacteriophage therapies. However, only recent advances in the areas of genome sequence analysis and bioinformatics as well as improved protocols to purify large quantities of bacteriophages, see for example EP2195418 or Smrekar et al. 2011 (Smrekar et al. 2011. J. Sep. Sci. 34:2152-58), made it possible for bacteriophages to also realize their potential in the Western World (Monk et al. 2010. Lett. Appl. Microbiol. 51:363-9).

It is the scope of this invention to provide natural, safe and efficient methods to fight *Salmonella* spp. in the entire value chain from farm to fork. The proposed methods are based on the use of specific bacteriophages to specifically and efficiently fight their natural host bacteria. Furthermore, the aim of the present invention is to provide new bacteriophages useful against microorganisms, in particular, *Salmonella* spp.

SUMMARY OF THE PRESENT INVENTION

In a first aspect, the present invention relates to compositions comprising at least one of the bacteriophages RMP9, ELB17.3, MP82.2, and FV7M4.14. The bacteriophage ELB17.3 comprises the sequence of Seq. ID No. 1 or upon performing PCR reactions using primer set 1 of Seq. ID No. 5 and Seq. ID No. 6, generating a fragment with the length of 492 bp or primer set 2 of Seq. ID No. 13 and Seq. ID No. 14, generating a fragment length of 632 bp. The bacteriophage MP82.2 comprising the sequence of Seq. ID No. 2 or upon performing PCR reactions using primer set 1 of Seq. ID No. 7 and Seq. ID No. 8, generating a fragment with the length of 1194 bp or primer set 2 of Seq. ID No. 15 and Seq. ID No. 16, generating a fragment with the length of 495 bp. The bacteriophage RMP9 comprises a sequence of Seq. ID No. 3 or upon performing PCR reactions using primer set 1 of Seq. ID No. 9 and Seq. ID No. 10, generating a fragment with the length of 820 bp or primer set 2 of Seq. ID No. 17 and Seq. ID No. 18, generating a fragment with a length of 528 bp. The bacteriophage FV7M4.14 comprising the sequence of Seq. ID No. 4 or upon performing PCR reactions using primer set 1 of Seq. ID No. 11 and Seq. ID No. 12, generating a fragment with the length of 584 bp or primer set 2 of Seq. ID No. 19 and Seq. ID No. 20, generating a fragment with the length of 1345 bp.

Said composition is useful as a vaccine against *Salmonella* infection as well as useful as a food processing aid for use in processing food.

Furthermore, said composition is particularly useful in prophylactically or therapeutically treating *Salmonella* infection in mammals including humans as well as in birds, in particular, livestock.

Moreover, the present invention relates to a method for fighting *Salmonella* comprising the step of treating matter suspected to be afflicted with *Salmonella* with a composition according to the present invention, in particular, for disinfecting surfaces containing or suspected to contain *Salmonella*. The method is particularly adapted to treat non-living matter.

Furthermore, the present invention relates to a method of treating or preventing *Salmonella* infection in mammals other than humans, or birds, in particular, livestock, comprising the step of administering a composition according to the present invention to said mammals other than humans, or birds, accordingly. Finally, the present invention relates to a method for determining the presence of the bacteriophages RMP9, MP82, ELB17, and FV7M4 or a progeny of said bacteriophages.

BRIEF DESCRIPTION OF THE DRAWINGS

FIG. 1: PCR-data of the four newly identified bacteriophages with primer set 1 showing individual sizes of PCR products, thus allowing the identification and differentiation of the bacteriophages, are provided.

FIG. 2: FIG. 2 shows the PCR identification assay with primer set 2 for the four newly isolated bacteriophages.

FIG. 3: The growth inhibition assay is described in the text. The results shown for a single phage, ELB17.3 are the average of at least three independent measurements.

FIG. 4: The growth inhibition assay is described in the text. The results shown for a phage cocktail containing ELB17.3, MP82.2, RMP9 and FV7M4.14 are the average of at least three independent measurements.

DETAILED DESCRIPTION OF THE PRESENT INVENTION

In a first aspect, the present invention provides a composition of at least one of the bacteriophages RMP9, ELB17.3, MP82.2, and FV7M4.14, whereby the bacteriophage ELB17.3 being deposited with the DSMZ with the deposition No. 26158 and can be identified by the presence of the sequence of Seq. ID No. 1 or upon performing PCR reactions using primer set 1 of Seq. ID No. 5 and Seq. ID No. 6, generating a fragment with the length of 492 bp or primer set 2 of Seq. ID No. 13 and Seq. ID No. 14, generating a fragment length of 632 bp, the bacteriophage MP82.2 being deposited with the DSMZ with the deposition No. 26173 and can be identified by the presence of the sequence of Seq. ID No. 2 or upon performing PCR reactions using primer set 1 of Seq. ID No. 7 and Seq. ID No. 8, generating a fragment with the length of 1194 bp or primer set 2 of Seq. ID No. 15 and Seq. ID No. 16, generating a fragment with the length of 495 bp, the bacteriophage RMP9 being deposited with the DSMZ with the deposition No. 26157 and can be identified by the presence of sequence of Seq. ID No. 3 or upon performing PCR reactions using primer set 1 of Seq. ID No. 9 and Seq. ID No. 10, generating a fragment with the length of 820 bp or primer set 2 of Seq. ID No. 17 and Seq. ID No. 18, generating a fragment with a length of 528 bp, the bacteriophage FV7M4.14 being deposited with the DSMZ under the deposition No. 26125 and can be identified by the presence of the sequence of Seq. ID No. 4 or upon performing PCR reactions using primer set 1 of Seq. ID No. 11 and Seq. ID No. 12, generating a fragment with the length of 584 bp or primer set 2 of Seq. ID No. 19 and Seq. ID No. 20, generating a fragment with the length of 1345 bp.

The bacteriophage deposited at the DSMZ under the deposition No. 1 26125 is identified herein synonymously as bacteriophage FV7M4.14 or FVM4.

The bacteriophage deposited at the DSMZ under the deposition No. 1 26157 is identified herein as bacteriophage RMP9.

The bacteriophage deposited at the DSMZ under the deposition No. 1 26158 is identified herein synonymously as bacteriophage ELB17.3 or ELB17.

The bacteriophage deposited at the DSMZ under the deposition No. 1 26173 is identified herein synonymously as bacteriophage MP82.2 or MP82.

As used herein, the term "comprise" or "comprising" as well as "contain" or "containing" includes the embodiments of "consist of" or "consisting of".

Moreover, the term "mammals" includes generally humans unless otherwise indicated.

As used herein, the term "or progeny of said bacteriophage" refers to bacteriophages stemming from or derived from the strains deposited at the DSMZ as identified.

The term "livestock" includes in particular poultry as well as pigs and cattle.

Further, the term "*Salmonella*" and "*Salmonella* spp." are used interchangeably and refer to *Salmonella* in general.

That is, the present invention provides new bacteriophages useful in combating *Salmonella* infection or preventing the same.

In a first embodiment, the composition is in form of a nutritional supplement or a feed supplement containing the composition according to the present invention. Said nutritional supplement or feed supplement is particularly for feeding livestock including poultry and other animals.

The terms feed supplement, nutritional supplement or feed additive are used herein interchangeably unless otherwise indicated. The terms are to be understood as an ingredient or a mixture or combination of ingredients which can be mixed to a feed to fulfill one or more specific need(s). Typically, the feed supplement, nutritional supplement or feed additive according to the present invention is part of a diet.

In particular, the present invention is directed to the use of the feed additive as defined herein as additive to livestock feed, in particular, poultry feed. The feed additive according to the present invention can be fed in combination and mixture with any kind of feed suitable for the respective subject, e.g. livestock, but can also be fed separately. Typically, the feed additive is part of a diet. The feed additive may be a component of a feed product.

The feed product containing the feed additive according to the present invention may contain further suitable other components like cereal products, protein raw material, fiber raw material and lignocelluloses-containing raw material. Moreover, the feed product may contain at least one of the components selected from trace elements, vitamins, tallow, enzymes, minerals and common additives added to feed products especially for poultry.

In another embodiment, the feed additive according to the present invention may be provided by the drinking water.

Moreover, the composition according to the present invention may be used as a food processing aid for use in food processing.

That is, the composition according to the present invention may be used as a food processing aid in meat processing, in particular, meat processing of poultry and pork.

The composition according to the present invention which may be in form of a pharmaceutical composition may comprise additional suitable diluents, excipients and/or carriers the skilled person is well aware of.

That is, in preferred embodiments, the pharmaceutical composition further comprises pharmaceutical additives or auxiliary substances, preferably, a pharmaceutically acceptable carrier, excipient or diluent.

The term "pharmaceutical composition" means a composition suitable for pharmaceutical use in a subject or individual, including an animal or human. A pharmaceutical composition generally comprises an effective amount of an active agent or ingredient and a carrier, including e.g. a pharmaceutically acceptable carrier.

A "therapeutic treatment" is a treatment administered to a subject or an individual that displays symptoms or signs of pathology, disease, or disorder in which treatment is administered to the subject for the purpose of diminishing or eliminating those signs or symptoms of pathology, disease or disorder.

As used herein, the term "carrier" refers to a diluent, adjuvant, excipient or vehicle.

The composition comprising the compounds according to the present invention will be formulated, dosed, and administered in a fashion consistent with good medical practice. Factors for consideration in this context include the stage of the particular disease or disorder being treated, the particular mammal being treated, the clinical condition of the individual subject, the site of delivery of the agent, the method of administration, the scheduling of administration, and other factors known to medical practitioners. The effective amount of the agent to be administered will be governed by such considerations. The key factor in selecting an appropriate dose and scheduling is the result obtained, as indicated above. The compounds according to the present invention are administered by any suitable means, including parenteral, topical, subcutaneous, intraperitoneal, intrapulmonary, intranasal, and/or intralesional administration. Parenteral infusions include intramuscular, intravenous, intraarterial, intraperitoneal, or subcutaneous administration. Intrathecal administration is also contemplated.

"Therapeutically- or pharmaceutically-effective amount" as applied to the compositions of the instant invention refers to the amount of composition sufficient to induce a desired biological result. That result can be alleviation of the signs and markers, symptoms, or causes of a disease, or any other desired alteration of a biological system.

In vitro assays as well as animal models may optionally be employed to help identifying optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems. Preferably, the pharmaceutical composition is administered directly or in combination with an adjuvant.

The term "administered" means administration of a therapeutically effective dose of the aforementioned pharmaceutical composition comprising the active ingredient according to the present invention in form of salts and solvates thereof to an individual.

The pharmaceutical composition according to the present invention comprises the active ingredient as described herein and, optionally, a pharmaceutical acceptable carrier. Such pharmaceutical compositions comprise a therapeutically effective amount of the active ingredient as defined herein and, optionally, a pharmaceutically acceptable carrier. The pharmaceutical composition may be administered with a physiologically acceptable carrier to a patient, as described herein. Acceptable means that the carrier be acceptable in the sense of being compatible with the other ingredients of the composition and not be deleterious to the recipient thereof. In a specific embodiment, the term "pharmaceutically acceptable" means approved by a regulatory agency or other generally recognized pharmacopoeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatine, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, aerosols and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium, carbonate, etc. Examples of suitable pharmaceutical carriers are described in "Remington's Pharmaceutical Sciences" by E. W. Martin (18th ed., Mack Publishing Co., Easton, Pa. (1990)). Such compositions will contain a therapeutically effective amount of the aforementioned compounds, salts or solvates thereof, preferably in purified form, together with a suitable amount of carrier so as to provide the form for proper administration to the patient. The formulation should suit the mode of administration.

Typically, a pharmaceutically or therapeutically acceptable carrier is a carrier medium which does not interfere with the effectiveness of the biological activity of the active ingredients and which is not toxic to the host or patient.

In a preferred embodiment, the composition according to the present invention may contain additional bacteriophages, in particular, bacteriophages specific against pathogenic *Salmonella* isolates. Alternatively, the composition may comprise other active ingredients, like bacteriophages combating or preventing infection with other pathogenic organisms. Moreover, the composition may comprise additional components suitable for administration to the mammal except humans, and birds. The skilled person is well aware of suitable other ingredients which may be incorporated into the composition accordingly, like nutrients, etc.

Moreover, the composition according to the present invention is particularly useful as a vaccine against *Salmonella* infection or for use in prophylactically or therapeutically treating *Salmonella* infection in mammals, including humans, and birds.

In a preferred embodiment, the composition according to the present invention is useful in preventing or treating foodborne diseases, disorders or conditions caused by *Salmonella*.

It is particularly preferred, that the composition according to the present invention is a composition containing the bacteriophage RMP9 with the deposition No. DSM 26157, the bacteriophage FV7 with the deposition No. DSM 26125, the bacteriophage ELB17 with the deposition No. DSM 26158, and the bacteriophage MP82 with the deposition No. DSM 26173.

The present invention provides in addition a method for fighting *Salmonella*. Said method is directed to comprise the step of treating said matter suspected to be afflicted or contaminated with *Salmonella* with the composition according to the present invention. In particular, said matter is non-living matter. For example, said method is a method for disinfecting surfaces containing or contaminated with or suspected to contain or to be contaminated with *Salmonella*.

Furthermore, a method is provided useful for treating feed, in particular livestock feed or matter in contact with mammals or birds, in particular livestock.

In addition, a method of treating or preventing *Salmonella* infection in mammals other than humans, or birds, in particular, livestock is provided. Said method comprises the step of administering a composition according to the present invention to mammals other than humans, or birds.

Said method is particularly useful for treating or preventing *Salmonella* infection in livestock like poultry. The way of administration can be determined easily by the skilled person. For example, the way of administration is performed by adding said composition to the feed, including water for drinking of the livestock.

Of course, other ways of administration are possible, including systemic or local administration. The skilled person is well aware of suitable rules of administration, in particular, when using said composition as a vaccine for vaccination against *Salmonella* infection.

As used herein, the term "treating or preventing" includes the eradication of *Salmonella* as well as reducing the load with *Salmonella* or other pathogenic organisms in the animal.

Moreover, the present invention relates to a method for determining the presence of at least one of the bacteriophages RMP9, MP82, ELB17, and FV7M4 or a progeny of said bacteriophages, comprising the steps of:

determining the presence of the sequence of Seq. ID No. 3 or upon performing PCR reactions using primer set 1 of Seq. ID No. 9 and Seq. ID No. 10, generating a fragment with the length of 820 bp or primer set 2 of Seq. ID No. 17 and Seq. ID No. 18, generating a fragment with a length of 528 bp specific for the presence of the bacteriophage RMP9 being deposited with the DSMZ with the deposition No. 26157; and/or determining the presence of the sequence of Seq. ID No. 2 or upon performing PCR reactions using primer set 1 of Seq. ID No. 7 and Seq. ID No. 8, generating a fragment with the length of 1194 bp or primer set 2 of Seq. ID No. 15 and Seq. ID No. 16, generating a fragment with the length of 495 bp specific for the presence of the bacteriophage MP82 being deposited with the DSMZ with the deposition No. 26173; and/or determining the presence of the sequence of Seq. ID No. 1 or upon performing PCR reactions using primer set 1 of Seq. ID No. 5 and Seq. ID No. 6, generating a fragment with the length of 492 bp or primer set 2 of Seq. ID No. 13 and Seq. ID No. 14, generating a fragment length of 632 bp specific for the bacteriophage ELB17 being deposited with the DSMZ with the deposition No. 26158, and/or determining the presence of the sequence of Seq. ID No. 4 or upon performing PCR reactions using primer set 1 of Seq. ID No. 11 and Seq. ID No. 12, generating a fragment with the length of 584 bp or primer set 2 of Seq. ID No. 19 and Seq. ID No. 20, generating a fragment with the length of 1345 bp specific for the bacteriophage FV7M4 being deposited with the DSMZ with the deposition No. 26125;

whereby the detection of at least one of the sequences of Seq. ID No. 1, Seq. ID No. 2, Seq. ID No. 3, or Seq. ID No. 4 or of the fragments generated as identified above is indicative for the presence of at least one of the bacteriophages RMP9, MP82, ELB17, and FV7M4 or a progeny of said bacteriophages.

The method may be useful in the field of food monitoring or food control or for surveillance of sheds or drove of livestocks, like poultries, The isolation of bacteriophages from nature follows a state of the art procedure known to any skilled microbiologist. Bacteriophages specific against pathogenic *Salmonella* isolates can be found with high frequency in the feces of both healthy and ill animals and humans, in the waste water of farms, in the sewer, in sewage treatment plants and in polluted rivers. Samples from such sources are collected, processed, and analyzed for the presence of *Salmonella*-specific bacteriophages. Briefly, liquid samples are sterile filtered, solid samples are homogenized in a suitable liquid and then sterile filtered. The resulting liquid samples are analyzed directly, without enrichment, in plaque test assays. In a petridish containing solid agar culture medium for bacterial growth, a mixture of host bacteria and the liquid sample to be analyzed are spread in a layer of soft agar. The petri dish is then incubated for 12 to 18 hours at 37 C. During this time the host bacteria will grow rapidly and start to form an opaque bacterial lawn on the soft agar. If a specific bacteriophage is present in the sample to be analyzed, it will also start to grow. To do so a bacteriophage hijacks a bacterial cell, produces approximately 100 progeny bacteriophages within that bacterium and then destroys the bacterium in order to release the progeny. The progeny will repeat the process, each hijacking a bacterial cell in the vicinity. As with every round of bacteriophage propagation more and more host bacteria will be destroyed, a hole, large enough to be seen by the naked eye, will start to appear in the bacterial lawn, a so called plaque. Each such plaque indicates the initial presence of a single bacteriophage able to grow on the chosen bacterial host and contains $10^6$ to $10^{10}$ bacteriophage particles. These progeny particles can be isolated from the soft agar by elution in an appropriate buffer, and represent the starting stock of a newly isolated bacteriophage.

Special focus lies on the determination of the propagation strategy of a newly isolated bacteriophage. Lytic bacteriophages use a single propagation strategy that results in the destruction of the host bacterium. Temperate bacteriophages, posses an alternative propagation strategy, in addition to the one used by lytic bacteriophages. While using this alternative strategy of propagation the temperate bacteriophage does not only keep the host bacterium alive and healthy, but also provides it with an insensitivity mechanism against infections by other bacteriophage particles of the same type. As surviving and insensitive bacteria would torpedo any attempt to eliminate a bacterial infection using bacteriophages, it is imperative to clearly distinguish between lytic and temperate bacteriophages and only use the former.

Historically the distinction was made in plaque test assays. Lytic bacteriophages produce clear plaques in such an assay, as they destroy all the host bacteria. Temperate bacteriophages on the other hand form turbid plaques, as some bacteria are kept alive, become insensitive and continue to grow. However, this distinction method shows a high rate of failure, as variants of temperate bacteriophages, so called virulent mutants, also form clear plaques and thus mimic the behavior of lytic bacteriophages.

Thus the only reliable method to distinguish lytic from temperate bacteriophages is to completely determine the nucleotide sequence of the genome of candidate bacteriophages, followed by a stringent bioinformatical analysis. The presence or absence of certain key genes coding for example for repressors, integrases or partitioning components makes it possible to clearly distinguish strictly lytic bacteriophages from their temperate and virulent relatives. In addition it is also possible to identify bacteriophages that carry genes coding for potential virulence factors or toxins. Such bacteriophages would pose a potential risk when produced in large numbers for practical applications and should thus be avoided.

Four novel bacteriophages, named ELB17.3, MP82.3, RMP9 and FV7M4.14, with specificity against *Salmonella* spp. were isolated from nature. A morphological characterization of the isolated bacteriophages by electron microscopy identified them as tailed bacteriophages belonging to the families Myoviridae and Syphoviridae (H.-W. Ackermann, 2006, 5500 Phages examined in the electron microscope. Archives of Virology 152:227-243.). The morphological features of a bacteriophage, however, do not correlate with its propagation strategy, its species specificity and its host range and thus a more detailed characterization was performed to determine the suitability of the bacteriophages for the treatment of bacterial infections.

The complete genomes of the four bacteriophages disclosed in this invention were determined and analyzed. A summary of the results is provided in Table 1:

TABLE 1

Genome analysis summary

| Phage | Genome molecule | Size | Number of identified genes | Number of tRNA genes | Number of encoded ORFs with similarity to protein sequences in Genbank | Genome restriction digestion by EcoRV | Genome restriction digestion by HindIII |
|---|---|---|---|---|---|---|---|
| ELB17.3 | dsDNA | 241841 bp | 288 | 3 | 271 | ≥16 fragments | ≥14 fragments |
| MP82.2 | dsDNA | 138669 bp | 272 | 20 | 240 | ≥16 fragments | ≥14 fragments |
| RMP9 | dsDNA | 61148 bp | 85 | None | 71 | No cut | No cut |
| FV7M4.14 | dsDNA | 46741 bp | 89 | None | 82 | ≥13 fragments | No cut |

Partial DNA sequences of the isolated bacteriophage are given as Seq. ID No. 1 to 4 whereby Seq. ID No. 1 identifies bacteriophage ELB17.3, Seq. ID No. 2 identifies bacteriophage MP 82.2, Seq. ID No. 3 identifies bacteriophage RMP9, and Seq. ID No. 4 identifies bacteriophage FV7M4.14. The genomes of these four bacteriophages do not encode any functions involved in lysogeny as described above and were thus confirmed to be strictly lytic. In addition, no known toxin genes or bacterial virulence factors (Boyd & Brüssow, 2002, TRENDS in Microbiol. 10:521-9) were found, providing further indication of the suitability of these bacteriophages for practical applications.

A PCR based identification assay was developed to easily identify the four bacteriophages disclosed in this invention as well as to distinguish them from unrelated bacteriophages. The nucleotide sequences of the four genomes were used as a base to design unique and specific PCR primer sets. In standard PCR reactions, where the corresponding phage genomic DNA served as template, these primer sets can be used to amplify fragments of defined size. For example, as shown in FIGS. 1 and 2, a PCR reaction with ELB17.3 primer set 1 results in a 492 bp fragment and reaction with ELB17.3 primer set 2 results in a 632 bp fragment, respectively, when the genome of the bacteriophage ELB17.3 was used as template. Any unknown bacteriophage can now be identified as being ELB17.3 when a PCR assay of its genomic DNA with the ELB17.3 primer sets results in PCR fragments of 492 bp and 632 bp, respectively. The identity of MP82.2, RMP9 and FV7M4.14 can be verified in analogy to the example provided above for ELB17.3.

In order to be suitable for practical applications against *Salmonella* spp. it is important that a strictly lytic bacteriophage also shows a broad range of activity against epidemiologically relevant *Salmonella* isolates. In a standard plaque test assay the four bacteriophages disclosed in this invention were examined if they are able to recognize and destroy various *Salmonella* isolates. In Table 2

TABLE 2

Bacteriophage lytic activity against *Salmonella* isolates

| | Phage | ELB17.3 | MP82.2 | RMP9 | FV7M4.14 |
|---|---|---|---|---|---|
| Salmo- | *S. dublin* | + | + | | |
| nella | *S. virchow* | + | + | + | |
| strain | *S. enteritidis* | + | + | | |
| | *S. paratyphi* B | + | + | | + |
| | *S. java* | + | + | + | + |
| | *S. typhimurium* | + | + | + | + |
| | *S. indiana* | + | + | + | + |
| | *S. infantis* | + | + | + | |
| | *S. kiambu* | + | + | | |
| | *S. livingstone* | + | | + | |
| | *S. london* | + | + | | |
| | *S. saintpaul* | + | + | | + |
| | *S. gallinarum* | + | | + | |
| | *S. derby* | + | + | | |

"+" indicates that the bacteriophage efficiently grows on the respective bacterial strain, while no entry indicates that the bacteriophage does not grow on the respective bacterial strain. The results show that all four bacteriophages disclosed in this invention have a broad and overlapping host range, covering all tested relevant *Salmonella* isolates.

The efficiency by which a bacteriophage can interfere with the growth of a bacterial strain is shown in a growth inhibition assay. A fresh bacterial overnight culture of a *Salmonella* strain with the concentration of $5 \times 10^9$ bacteria per milliliter is serially diluted in two sets of 10 tubes, each containing fresh growth medium. Each consecutive tube contains 10 fold less bacteria, with the last two tubes per set containing 5 and 0 bacteria per milliliter, respectively. To assay the effect of the presence of a bacteriophage, the first set of 10 tubes is then spiked with a bacteriophage solution to an end concentration of $10^6$ bacteriophages per milliliter. As a control the second set of 10 tubes is spiked with an equal volume of growth medium. Both sets of tubes are then incubated overnight (16 h) at 37° C. In both sets the diluted bacteria will start to grow. In the control set the bacteria remain undisturbed and eventually reach their stationary phase concentration of $5 \times 10^9$ bacteria per milliliter. Also the second to last tube containing only 5 bacteria per milliliter reaches this stationary phase concentration overnight. Only the last tube of the control stays clear, as it does not contain any bacteria. However, when bacteriophages are added, they recognize and destroy bacterial cells and thus inhibit or slow the growth of the bacterial population. This effect is demonstrated by measuring the optical density at 600 nm, which detects the turbidity of a culture, which in turn is an indication of the cell density. FIG. 3 shows such a growth inhibition assay for a single bacteriophage, in our example ELB17.3 growing on a *S. typhimurium* host. The data show that the bacteriophage manages to eliminate small amounts of bacteria in the range of 5 to 500 cells per milliliter. However, if the initial number of bacteria exceeds 5000 cells per milliliter the onset of residual growth can be observed, indicating that not all bacteria are killed instantly. Nevertheless, even at the highest starting concentrations of bacteria the killing effect of the bacteriophages is observed, as the bacterial cultures do not reach the stationary phase concentrations of the control within the time frame of the assay (16 h).

FIG. 4 shows a growth inhibition assay in which a bacteriophage cocktail containing the four bacteriophages, disclosed in this invention, was analyzed. In order to be able to compare this second assay to the previous, the total bacteriophage concentration was kept constant at $10^6$ bacteriophages per milliliter. The individual phage concentrations of ELB17.3, FV7M4.14, RMP9 and MP82.2 were thus only $2.5 \times 10^5$ per milliliters. The results show that the bacteriophage cocktail performs close to a 100 fold better than a single bacteriophage alone, effectively inhibiting the growth of up to 50.000 bacterial cells per milliliter.

Jointly these results show that bacteriophages in general perform best when used as a preventive measure, as they efficiently and effectively eliminate small amounts of bacteria. Though they do also show effects in the presence of large concentrations of bacteria, the outcome of such intervention strategies is less predictable. Furthermore, the results indicate that it is preferable to use a combination of distinct bacteriophages in a cocktail over the treatment with a single bacteriophage.

In one embodiment of the present invention broiler chickens were fed with a cocktail of bacteriophages containing a total of seven bacteriophages, including the bacteriophages ELB17.3, MP82.2, RMP9 and FV7M4.14 disclosed in this invention. Chicks, freshly hatched, were placed in a coop with known history of *S. parathyphi* B contamination. The birds were separated into several groups, some of them serving as untreated controls while others received the bacteriophage cocktail via the water. Every week several birds of each group were sacrificed and analyzed for the presence of *Salmonella* in the appendix and liver. Birds from the untreated control groups were infected by *S. parathyphi* B. Treated birds, on the other hand, stayed *Samonella*-free throughout the entire six week fattening cycle.

Poultry sheds with longstanding history of *Salmonella* spp contamination were selected to study the efficacy and efficiency of bacteriophage cocktails containing the bacteriophages according to the present invention, RMP9, ELB17.3, MP82.2, and FV7M4.14. Trials with both chickens and turkeys were done under regular poultry production conditions. Standard sheds for chickens contained up to 40.000 birds, standard sheds for turkeys up to 6.000 birds. Different sheds were known to be contaminated with different *Salmonella* isolates like *Salmonells paratyphi* B (Java), *Salmonella typhimurium*, *Salmonella infantis*, *Salmonella Newport* and *Salmonella saintpaul*. The birds received a constant concentration of bacteriophage cocktail in the water for drinking during the entire fattening cycle. The final analyses by the slaughterhouses (compulsory routine analyses) demonstrated that the bacteriophage cocktails used were successfully preventing the infection of the birds by *Salmonella* spp, resulting in *Salmonella* free birds and *Salmonella* free poultry meat.

The invention claimed is:

1. A composition comprising the bacteriophages RMP9, MP82, ELB17, and FV7M4 or a progeny of said bacteriophages, wherein the bacteriophage RMP9 is deposited with the DSMZ with the deposition No. 26157 and can be identified by the presence of the sequence of Seq. ID No. 3 or upon performing PCR reactions using primer set 1 of Seq. ID No. 9 and Seq. ID No. 10, generating a fragment with the length of 820 bp or primer set 2 of Seq. ID No. 17 and Seq. ID No. 18, generating a fragment with a length of 528 bp, the bacteriophage MP82 is deposited with the DSMZ with the deposition No. 26173 and can be identified by the presence of the sequence of Seq. ID No. 2 or upon performing PCR reactions using primer set 1 of Seq. ID No. 7 and Seq. ID No. 8, generating a fragment with the length of 1 194 bp or primer set 2 of Seq. ID No. 15 and Seq. ID No. 16, generating a fragment with the length of 495 bp, the bacteriophage ELB17 is deposited with the DSMZ with the deposition No. 26158 and can be identified by the presence of the sequence of Seq. ID No. 1 or upon performing PCR reactions using primer set 1 of Seq. ID No. 5 and Seq. ID No. 6, generating a fragment with the length of 492 bp or primer set 2 of Seq. ID No. 13 and Seq. ID No. 14, generating a fragment length of 632 bp, and the bacteriophage FV7M4 is deposited with the DSMZ with the deposition No. 26125 and can be identified by the presence of the sequence of Seq. ID No. 4 or upon performing PCR reactions using primer set 1 of Seq. ID No. 11 and Seq. ID No. 12, generating a fragment with the length of 584 bp or primer set 2 of Seq. ID No. 19 and Seq. ID No. 20, generating a fragment with the length of 1345 bp.

2. The composition according to claim 1 further comprising suitable diluents, excipients and/or carriers.

3. The composition according to claim 1 further containing other bacteriophages.

4. A method for fighting *Salmonella* comprising the step of treating matter suspected to be afflicted with *Salmonella*, with a composition comprising at least one bacteriophage as set forth in claim 1.

5. The method according to claim 4 for treating food or matter being in contact with mammals or birds.

6. A method of treating or preventing *Salmonella* infection, in mammals, comprising the step of administering a composition comprising at least one bacteriophage as set forth in claim 1 to mammals.

7. The method according to claim 6, wherein said composition is administered as a vaccine against *Salmonella* infection.

8. The method according to claim 6 comprising the step of administering the composition by feed including water for drinking.

9. A method for detecting at least one of the bacteriophages RMP9, MP82, ELB17, and FV7M4 or a progeny of said bacteriophages, comprising the steps of:

detecting the sequence of Seq. ID No. 3 or upon performing PCR reactions using primer set 1 of Seq. ID No. 9 and Seq. ID No. 10, generating a fragment with the length of 820 bp or primer set 2 of Seq. ID No. 17 and Seq. ID No. 18, generating a fragment with a length of 528 bp specific for the presence of the bacteriophage RMP9 being deposited with the DSMZ with the deposition No. 26157; and/or detecting the sequence of Seq. ID No. 2 or upon performing PCR reactions using primer set 1 of Seq. ID No. 7 and Seq. ID No. 8, generating a fragment with the length of 1194 bp or primer set 2 of Seq. ID No. 15 and Seq. ID No. 16, generating a fragment with the length of 495 bp specific for the presence of the bacteriophage MP82 being deposited with the DSMZ with the deposition No. 26173; and/or detecting the sequence of Seq. ID No. 1 or upon performing PCR reactions using primer set 1 of Seq. ID No. 5 and Seq. ID No. 6, generating a fragment with the length of 492 bp or primer set 2 of Seq. ID No. 13 and Seq. ID No. 14, generating a fragment length of 632 bp specific for the bacteriophage ELB17 being deposited with the DSMZ with the deposition No. 26158, and/or detecting the sequence of Seq. ID No. 4 or upon performing PCR reactions using primer set 1 of Seq. ID No. 11 and Seq. ID No. 12, generating a fragment with the length of 584 bp or primer set 2 of Seq. ID No. 19 and Seq. ID No. 20, generating a fragment with the length of 1345 bp specific for the bacteriophage FV7M4 being deposited with the DSMZ with the deposition No. 26125;

whereby the detection of at least one of the sequences of Seq. ID No. 1, Seq. ID No. 2, Seq. ID No. 3, or Seq. ID No. 4 or of the fragments generated as identified above is indicative for the presence of at least one of the bacteriophages RMP9, MP82, ELB17, and FV7M4 or a progeny of said bacteriophages.

10. The method of claim 4, wherein said matter is a surface containing or suspected to contain *Salmonella* and said step of treating disinfects said surface.

11. The method of claim 5, wherein said food is livestock feed.

12. The method of claim 5, wherein said mammals or birds are livestock.

13. The method of claim 6, wherein said mammals are livestock.

14. The method according to claim 13 wherein the livestock is poultry.

15. The method of claim 6, wherein said mammals do not include humans or birds.

* * * * *

SEQUENCE LISTING

<160> NUMBER OF SEQ ID NOS: 20

<210> SEQ ID NO 1
<211> LENGTH: 750
<212> TYPE: DNA
<213> ORGANISM: bacteriophage

<400> SEQUENCE: 1

```
gcgtgcgctg gcgcgcctcg gtacagttgg tcaaccaatg cgtgatactt tttgagtatc    60
gatagtacat ctgagccatc aggggccaca atgactgctc ctggaagagc cctaaaagac   120
actttatcgc cgatgctgct gatgtgacgg aaacggaagt ccgttttgcg atccagtttc   180
gacgcaatac ccagttgtgt aaatctggct gcaaactcgg ccggcggatt attcatatcc   240
atcaacgaat gtaaaacaac tttcgaatcc tgcgtaatag tcaactcgat ggtgtgggcg   300
gcgcgtttac ggtcaatggt aactgtaaaa ggcttcttga agaaatcaat cccaaccggc   360
aaagttgccc agacgaacgt ttcttctttg tcagacgtgt cgtaggtaat taggaagcgg   420
aaagtgttac cgttaacaag ttcaagcgat gcgttgcaga aaggcgagcc ccagtacccg   480
ataagtgtga accaccagta cggcgtagtg gttgtcgagt agtaacttgg taatgtatac   540
gtcgcctgga acttatagtc actaagagaa tacctccatg accctaagat gctatactgg   600
tcagctttgt tcgtattagt aacgaagcca ccggcgttat cgtacgtaaa gttcggttca   660
attaaaccgt tatcaacata ggttgcggtg ttatttgcca tcggatcggg tatcggcggt   720
aatgtcgcga tcttctgtcc gatctcggca                                    750
```

<210> SEQ ID NO 2
<211> LENGTH: 1100
<212> TYPE: DNA
<213> ORGANISM: bacteriophage

<400> SEQUENCE: 2

```
ttatacgcgc ggctgcttcg gtagagcggc tgcgtcagtt gcttcacgaa ctttgattct    60
ataagccttc cagttttga gtgccatcac ctctccctta gtcgcggatt ccacatccac   120
cttgtcctgg tactgtgcaa tcttctcatt tgctacggca agtaggcgtt gtttctgtgc   180
atccagatcc cgtgtaatat actcaggatt gatatcaaat ttcaacgtct ttggatcaaa   240
aagatatttc tgacctaatg cgagatcatc cggcaccttt ttagccggga cttcaattaa   300
agaggcacct gctgggtaca gagaacttgc atctgtagaa aaaccagtaa caaccccatc   360
agagtaaagg acttttactg tatcttcttt catctcttta agagcttcat agaagtcaac   420
cccatcttct gaacgaaaga aggtgacccc aaacagggcc agttcttcag aaattttctc   480
tggggtgtag acttctacgt ttttaagatg taccatctgg cctcctctta taattgtccg   540
atagtgtacc aaccgccgtt gatatacttc tggatcggtc ttgaataaat atcaacgaac   600
tcatcttgct tgtgactggc tgaccagatg ttaaaacctg tcaccatgca accacctgcg   660
gctcggtaca caaaagattc cctaccgaga ctgcttcgag gtgttgaaat ttctgatcca   720
agtcggatat cctgcacccc ttgaggcggc agggcaaggg ttaagttacc gttaccatct   780
gctgtcgcac cgttcactgc acgaacaacg ttcctaccac caactactgc gctttgacta   840
ctaacagtaa gggagccggt tgttgtgttg ccatttacct gtgcattact tgcagtgatc   900
tttacaggaa ccaccaggtt ctgaatcgta ctgttggtag cattcatcgt tccggcagtt   960
gctgtcccgt tcaccgtaag gttctgggta gtagtgttcg ttgcactaat tgttgaaatc  1020
gttgctgtgc ttgtcaccgt caggtttgtt gcgcgagcgg tggttgactg caatgtgttc  1080
gttgtgatag tgttagaaac                                              1100
```

<210> SEQ ID NO 3
<211> LENGTH: 535
<212> TYPE: DNA
<213> ORGANISM: bacteriophage

```
<400> SEQUENCE: 3
gattgccatg aaaaacaagg atttaactgg aaagacgttt aatcgactca cggtaattcg      60
gctatccgat ttaccgtcat cgcgcactaa cccgcgaaaa tggatatgca gatgtgtatg     120
cggtgaaaac acacttgttg gcacgagaga gttaatctcc gggagaaaga aaagctgcgg     180
gtgtttatta cgagaatcat cgcgcgaaag gatgcggaag atgaaaacaa acacggttg      240 ttccggcgag aggctatata acgtttggcg gtcaatgaaa tcccggtgtc atcgcgaaac     300
agacccggat tattgttact acggcgcaag aggggtggcc gtttgcgatc gctggcggga     360
aagctattcg gcatttaaag aagacgtggg cggcgggtgg aaacaagggc tgacgctcga     420
ccgcatagac aacgacggtc attacgaacc cggaaatgtc aagtggtcaa cgatgacgga     480
gcaggcgttg aaccgcagac ctagagggtc ggttttttcct acgcggagaa accaa         535

<210> SEQ ID NO 4
<211> LENGTH: 350
<212> TYPE: DNA
<213> ORGANISM: bacteriophage

<400> SEQUENCE: 4
tcgcgcctta caattgcttg tgagggatct tgttgtaaga atgcgccgta acacaaagcg      60
ccttaaattt gatgatcagg ttagtgaagc ggcggcagat aatgaatcat acgcagagga     120
attaatttcc gcattcattg cgctactgcc aactttcgcg ctatccatct ataaattcaa     180
ctcaaatgaa tttatcagga tcgcaaataa gactggaggc aagaataatt tagccgtcct     240
gttgctgatt ggtctagggg ctaacgctgg tgaatcgtgg tacgcgccta aatatcacgt     300
atggcggcaa atggtgcgcg actctatcag aaagatggtt gacaatattc                350

<210> SEQ ID NO 5
<211> LENGTH: 20
<212> TYPE: DNA
<213> ORGANISM: artificial
<220> FEATURE:
<223> OTHER INFORMATION: synthetic oligonucleotide

<400> SEQUENCE: 5
tgggagcgct gtcaccatca                                                   20

<210> SEQ ID NO 6
<211> LENGTH: 22
<212> TYPE: DNA
<213> ORGANISM: artificial
<220> FEATURE:
<223> OTHER INFORMATION: synthetic oligonucleotide

<400> SEQUENCE: 6
cgactctggc aggatttgaa cc                                                22

<210> SEQ ID NO 7
<211> LENGTH: 20
<212> TYPE: DNA
<213> ORGANISM: artificial
<220> FEATURE:
<223> OTHER INFORMATION: synthetic oligonucleotide

<400> SEQUENCE: 7
ttggagggct aggccattta                                                   20
```

```
<210> SEQ ID NO 8
<211> LENGTH: 21
<212> TYPE: DNA
<213> ORGANISM: artificial
<220> FEATURE:
<223> OTHER INFORMATION: synthetic oligonucleotide

<400> SEQUENCE: 8
caacggtcgg tggtgcgttt a                                              21

<210> SEQ ID NO 9
<211> LENGTH: 20
<212> TYPE: DNA
<213> ORGANISM: artificial
<220> FEATURE:
<223> OTHER INFORMATION: synthetic oligonucleotide

<400> SEQUENCE: 9
gacgaaagcg gcacggcaac                                                20

<210> SEQ ID NO 10
<211> LENGTH: 20
<212> TYPE: DNA
<213> ORGANISM: artificial
<220> FEATURE:
<223> OTHER INFORMATION: synthetic oligonucleotide

<400> SEQUENCE: 10
cgcatgtatg ccgggcctgt                                                20

<210> SEQ ID NO 11
<211> LENGTH: 21
<212> TYPE: DNA
<213> ORGANISM: artificial
<220> FEATURE:
<223> OTHER INFORMATION: synthetic oligonucleotide

<400> SEQUENCE: 11
gagcggttgc cacgttcaaa g                                              21

<210> SEQ ID NO 12
<211> LENGTH: 20
<212> TYPE: DNA
<213> ORGANISM: artificial
<220> FEATURE:
<223> OTHER INFORMATION: synthetic oligonucleotide

<400> SEQUENCE: 12
tattgcagcg cgtcaacctg                                                20

<210> SEQ ID NO 13
<211> LENGTH: 20
<212> TYPE: DNA
<213> ORGANISM: artificial
<220> FEATURE:
<223> OTHER INFORMATION: synthetic oligonucleotide

<400> SEQUENCE: 13
tgtgcgtgta ccgggtggtt                                                20

<210> SEQ ID NO 14
<211> LENGTH: 20
<212> TYPE: DNA
<213> ORGANISM: artificial
<220> FEATURE:
<223> OTHER INFORMATION: synthetic oligonucleotide
```

-continued

```
<400> SEQUENCE: 14
tcaagccgcg caacaactcc                                              20

<210> SEQ ID NO 15
<211> LENGTH: 21
<212> TYPE: DNA
<213> ORGANISM: artificial
<220> FEATURE:
<223> OTHER INFORMATION: synthetic oligonucleotide

<400> SEQUENCE: 15
gtctgcggtg accgtctgca a                                            21

<210> SEQ ID NO 16
<211> LENGTH: 22
<212> TYPE: DNA
<213> ORGANISM: artificial
<220> FEATURE:
<223> OTHER INFORMATION: synthetic oligonucleotide

<400> SEQUENCE: 16
ggatgccttg ggtctgggaa ct                                           22

<210> SEQ ID NO 17
<211> LENGTH: 20
<212> TYPE: DNA
<213> ORGANISM: artificial
<220> FEATURE:
<223> OTHER INFORMATION: synthetic oligonucleotide

<400> SEQUENCE: 17
tgccaaagcg ggtcgaatgc                                              20

<210> SEQ ID NO 18
<211> LENGTH: 20
<212> TYPE: DNA
<213> ORGANISM: artificial
<220> FEATURE:
<223> OTHER INFORMATION: synthetic oligonucleotide

<400> SEQUENCE: 18
accagccacg ccgagctatg                                              20

<210> SEQ ID NO 19
<211> LENGTH: 21
<212> TYPE: DNA
<213> ORGANISM: artificial
<220> FEATURE:
<223> OTHER INFORMATION: synthetic oligonucleotide

<400> SEQUENCE: 19
gagcggttgc cacgttcaaa g                                            21

<210> SEQ ID NO 20
<211> LENGTH: 20
<212> TYPE: DNA
<213> ORGANISM: artificial
<220> FEATURE:
<223> OTHER INFORMATION: synthetic oligonucleotide

<400> SEQUENCE: 20
atccgcgcgt ccaaacgttc                                              20
```